United States Patent [19]

Falck et al.

[11] Patent Number: 5,070,875
[45] Date of Patent: Dec. 10, 1991

[54] APPLANATION TONOMETER USING LIGHT REFLECTION TO DETERMINE APPLANATION AREA SIZE

[75] Inventors: Francis Y. Falck, Rochester, N.Y.; Robert W. Falck, Pawcatuck; Lawrence W. Engdahl, Guilford, both of Conn.

[73] Assignee: Falcken, Inc., Pawcatuck, Conn.

[21] Appl. No.: 615,083

[22] Filed: Nov. 19, 1990

[51] Int. Cl.$^5$ .............................................. A61B 3/16
[52] U.S. Cl. ..................................... 128/645; 128/652
[58] Field of Search ....................... 128/645, 646, 652; 351/221

[56] References Cited

U.S. PATENT DOCUMENTS

| | | | |
|---|---|---|---|
| 3,070,997 | 1/1963 | Papritz et al. | 128/652 |
| 3,150,521 | 9/1964 | Mackay et al. | 128/645 |
| 3,338,090 | 8/1967 | Coombs, Jr. et al. | 128/652 |
| 3,449,945 | 6/1969 | Mohrman | 128/652 |
| 3,449,946 | 6/1969 | Gabriel et al. | 73/80 |
| 3,651,689 | 3/1972 | Haddad | 73/80 |
| 3,832,891 | 9/1974 | Stuckey | 73/80 |
| 3,952,585 | 4/1976 | Perkins et al. | 128/652 |
| 3,977,237 | 8/1976 | Tesi | 73/80 |
| 4,164,863 | 8/1979 | Ragsdale | 128/652 |
| 4,523,597 | 6/1985 | Sawa et al. | 128/652 |

OTHER PUBLICATIONS

Brochure from Bio-Rad, Ophthalmic Division, Oculab Products, Showing "Tono-Pen", 1987, Glendale, California.

Primary Examiner—Randy C. Shay
Attorney, Agent, or Firm—Eugene Stephens & Associates

[57] ABSTRACT

A tonometer divides internally incident light at the applanating surface of a prism so that light incident in the applanation area is refracted into the eye and light incident around the applanation area is internally reflected within the prism. Infrared light is preferred for this, and the amount of the reflected light is detected to provide an objective indication of the size of the area that is applanated. This allows intraocular pressure to be determined objectively from the force difference applied to the prism to change the applanation area between reference and measurement sizes, both of which are reliably determined from previous calibration for the amount of the reflected light. Many variations are possible in applying a variable force to the applanating prism and on operating the instrument with the preferred microprocessor, which can also store, display, and manipulate relevant patient data.

49 Claims, 6 Drawing Sheets

APPLANATION TONOMETER USING LIGHT REFLECTION TO DETERMINE APPLANATION AREA SIZE

TECHNICAL FIELD

This invention involves an applanation tonometer for measuring intraocular pressure of the human eye.

BACKGROUND

Applanation tonometers have advantages over indentation and air puff tonometers, and applanation tonometers are available in several forms. They all require skillful operation to obtain consistent readings, and there has not yet been an applanation tonometer that is automatic enough to eliminate user skill as a variable. Present applanation tonometers also consume some operating time and require some subjective judgments in making readings, so that a truly automatic tonometer ought to operate faster and more reliably.

Our applanation tonometer is made to solve these problems and to operate rapidly in a truly automatic way so that pressure readings will not vary with user skill. We have also made our tonometer portable so that it can be used anywhere a pressure reading is desired. We have included a microprocessor in our tonometer so that it can calculate pressure readings, compare successive readings, store readings, communicate with a computer, and display pressure readings and related patient data. We have also made our tonometer usable in any orientation or attitude, whether mounted or hand held.

SUMMARY OF THE INVENTION

Our tonometer uses a different optical principle for determining the size of an applanated area of the cornea. The principle is Snell's Law of refraction, which our tonometer uses to divide light incident on an applanating prism surface so as to transmit a portion of the light through the prism surface in the applanated area and to reflect another portion of the light around the applanated area. Both portions vary with the size of the applanated area, and our tonometer detects one of the portions to determine when the applanated area reaches reference and measurement sizes. It then determines intraocular pressure from the difference in force required to change the cornea applanation from the reference size to the measurement size.

Our preferred way of exploiting optical refraction and reflection laws in an applanation tonometer is to direct light through a prism to be incident on an applanating surface of the prism at an angle that lets light pass through the prism surface and into the eye in the applanated area where the prism and the cornea are in wetted contact. The same incidence angle internally reflects all the light from around the applanated area where the prism surface is in contact with air. The reflected light also passes through the prism enroute to a detector that can determine the applanated area size from the amount of the reflected light. This allows accurate and objective determinations of applanated area in both reference and measurement sizes.

All that remains to determine intraocular pressure is to know the force required to change the applanated area from the reference to the measurement size, and this can be done in a number of ways. We prefer a counterbalanced and pivotally mounted prism pressed against the cornea by a spring whose position can be varied by a thumb wheel or a stepping motor. One of the advantages of such an arrangement is making the tonometer usable in any attitude. We also prefer a microprocessor for making and displaying the pressure determination and for intercommunicating this and other patient-related information with a computer.

DRAWINGS

FIGS. 1 and 2 schematically illustrate the preferred way that our tonometer divides light incident on the applanating surface of a prism to determine the size of the applanated area, with the prism of FIG. 1 applanating a corneal surface to a small, reference size, and with the prism of FIG. 2 applanating the corneal surface to a larger, measurement size.

FIG. 3 schematically shows a preferred embodiment of a prism cooperating with a light source and a detector for use in our tonometer.

FIG. 4 is a front elevational view of the applanating surface of the preferred prism of FIG. 3.

FIGS. 5 and 7 respectively show the preferred reference and measurement sizes for corneal areas applanated with our tonometer and for calibration surfaces for calibrating our tonometer.

FIGS. 6 and 8 respectively show reference and measurement size calibrating elements engaging the applanating surface of our tonometer prism for calibration purposes.

FIG. 9 schematically shows a simplified form of a preferred system for varying the force that presses our tonometer prism against an eye.

FIG. 10 schematically shows another prism pressing system.

Figure 14:
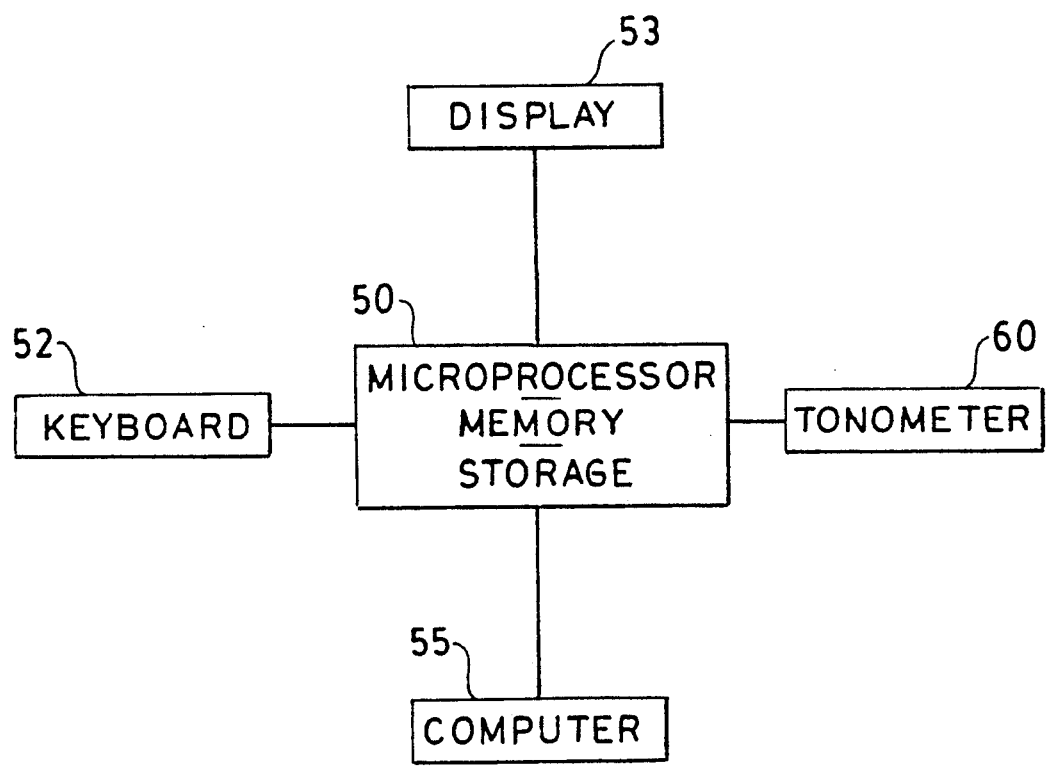

FIG. 14 schematically shows the interrelationships of a microprocessor for our tonometer with a display, keyboard, and computer.

DETAILED DESCRIPTION

Our tonometer objectively determines the size of an applanated area of the cornea. It does this by exploiting Snell's law of refraction which describes the trigonometric relationship between incidence and refraction angles that occur as light encounters an interface between two media having different refractive indexes. By choosing a suitable refractive index for a tonometer prism relative to the 1.0 index of refraction of air and the 1.33 index of refraction of water at the wetted surface of the cornea, and by using an appropriate wavelength of light at an appropriate incidence angle, our tonometer can transmit a portion of the incident light through the applanated area and can reflect another portion of the light around the applanated area. Either of these light portions is a function of the size of the applanated area, which can then be determined by the amount of light reaching a detector.

To accomplish this, we prefer a prism 10 made so that light directed toward the eye is internally incident on applanating surface 15. There, the internally incident light is divided into two portions—one that transmits through the applanated area into the eye, and one that reflects internally from surface 15 around the applanated area, where surface 15 is in contact with air. In other words, the internally incident light reflects completely from the portion of surface 15 that contacts air, with its 1.0 index of refraction, while the incident light passes through the wetted region where the cornea is applanated and presents an index of refraction of 1.33. Transmitting light through the applanated area and reflecting light around the applanated area effectively divides the incident light into two portions, both of which are functions of the size of the applanated area. In the preferred embodiment illustrated in FIGS. 1 and 2, the reflected light from around the applanated area is directed to a detector 11 that receives an amount of reflected light that is inversely related to the size of the applanated area.

We prefer using infrared light with our tonometer; and we have found that if prism 10 has an index of refraction of about 1.5, the infrared light can be made incident on applanating surface 15 at an angle of about 45°, to have the desired effect. Under these conditions, the light incident on applanating surface 15 is internally reflected wherever surface 15 is in contact with air, with its 1.0 index of refraction, and the light incident on applanating surface 15 in the area of applanating contact with cornea 20 is transmitted through surface 15 and refracted into the eye, where the index of refraction is about 1.33. This divides the light so that the size of the applanated area can be determined by the amount of the light reflected internally within prism 10.

When prism surface 15 touches cornea 20, the area of interengagement with the cornea (and a small meniscus ring around the engaged area) becomes wetted with water having an index of refraction of 1.33, which effectively allows incident IR light to transmit through applanating surface 15 and into cornea 20. The transmitted light is refracted as it passes into cornea 20; and within the eye, the transmitted IR light is scattered, reflected, and absorbed so that it does not pass back into prism 10. The light transmitted through applanating surface 15 into the eye subtracts from the light that is otherwise reflected from applanating surface 15, allowing the reduced amount of reflected light to indicate the size of the applanated area. For this work, we prefer that the light source 12 be strobed, rather than continuous, to reduce the power required and to help keep the instrument cool.

A tonometer can work in a similar way with light reflecting back out from the eye. This is technically more difficult and involves directing light into the eye so that it reflects back out to the cornea at a proper angle of incidence. The light used should not be infrared, which the eye tends to absorb and should preferably be in the visible spectrum. The index of refraction of the applanating prism also must be reduced. The outward bound light is directed onto the inside surface of the cornea at an incidence angle that internally reflects the light wherever the cornea is in contact with air and refractively transmits the light into the applanating prism in the area where the prism is in wetted contact with the cornea. This divides the incident light into a transmitted portion in the applanated area and a reflected portion around the applanated area, allowing the tonometer to determine the size of the applanated area from the amount of the transmitted portion, which is directed through the prism to a detector.

Although such a system is theoretically possible, we think it is much more difficult to implement, and we prefer our way of operating a tonometer by using IR light that is internally incident on applanating surface 15 of prism 10. Such operation is assumed in the description that follows.

We also have considered the possibility of using only a measurement size of applanation area and eliminating any reference size applanation area. Although this may introduce some error into the measurement, the error may be kept to an insignificant percentage by carefully adjusting the system that applies prism pressing force. Also, bare and unpressured contact of the prism with the cornea can serve as a reference, because light contact refracts some of the prism light into the eye. Altogether, though, we prefer using both a reference and a measurement size of applanation area for the increased accuracy such an arrangement can achieve.

Figure 3:
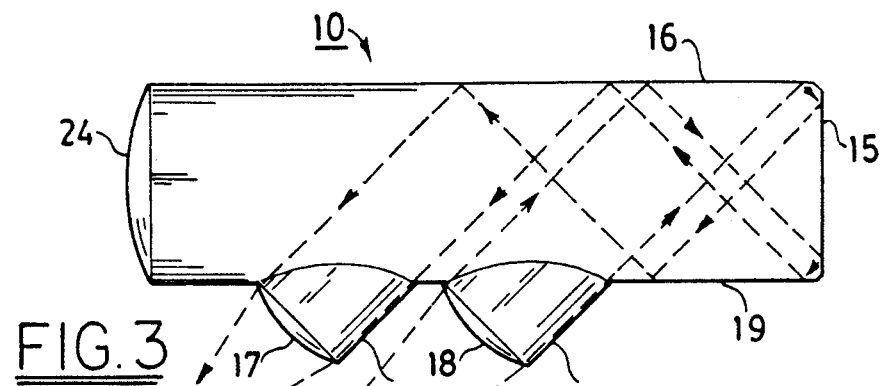

As shown in FIG. 3, we prefer expanding the functions of prism 10 by arranging a pair of side ports 13 and 14 with integrally molded lenses 17 and 18, paired respectively with a light source 12 and a detector 11. Source 12 is preferably a light-emitting diode that outputs an infrared beam. This is directed via lens 18 through port 14 to reflect off top surface 16 and be incident on applanating surface 15 at about a 45° angle. Top surface 16 is preferably made flat for this reflective purpose and can be given a reflective coating to ensure that the entire incoming beam is reflected. The light reflected from surface 15 around the applanated area reflects off bottom surface 19, which is also preferably flat and which can also have a reflective coating. The internally reflected light proceeds from reflecting surface 19 back up to top reflecting surface 16, which directs the reflected light through port 13 and lens 17 to detector 11, which is preferably a photo diode responsive to IR light.

Prism 10, which now serves as a multi-function optical element, is also preferably molded with an integral lens 24 on the surface opposite applanation surface 15 so that the user can look through lens 24 and focus on applanation surface 15, to view the engagement of surface 15 with cornea 20. This should not ordinarily be necessary, but can be used to help align applanating surface 15 with cornea 20.

Prism 10 is preferably molded of resin material in the preferred configuration so that it can be formed at low cost in large quantities. Prisms 10 are also preferably made to be easily removed and replaced, for sterility or other purposes.

Figure 4:
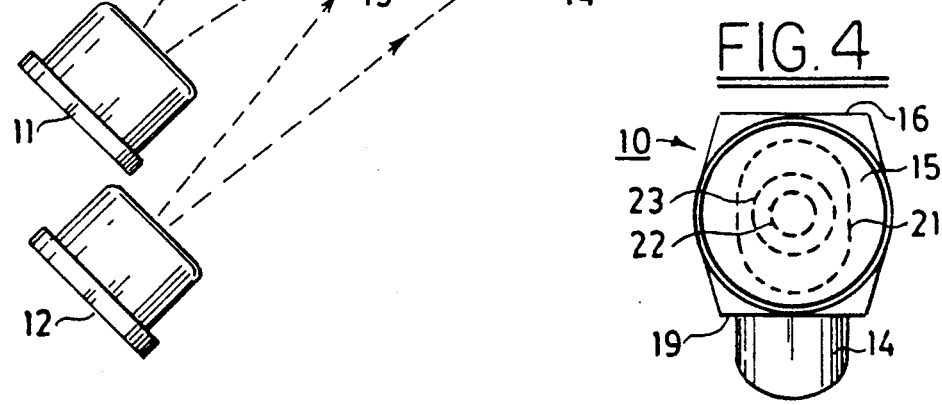

As shown in FIG. 4, the light pattern that is internally incident on applanating surface 15 is represented by the broken line oval 21, and broken line circles 22 and 23 respectively represent the sizes of reference and measurement applanation areas. All the internally incident light transmits through the reference area 22, when this area is in applanating contact with the cornea; and when the applanated area is enlarged to the measurement size, then all the light incident within the circle 23 is transmitted through applanated surface 15. The incident light outside of applanated areas 22 and 23 is internally reflected and directed to detector 11, which determines the size of the applanated area from the amount of the reflected light.

Figure 1:
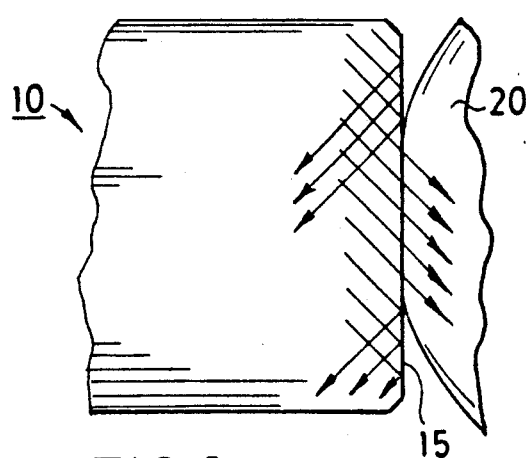
Figure 2:
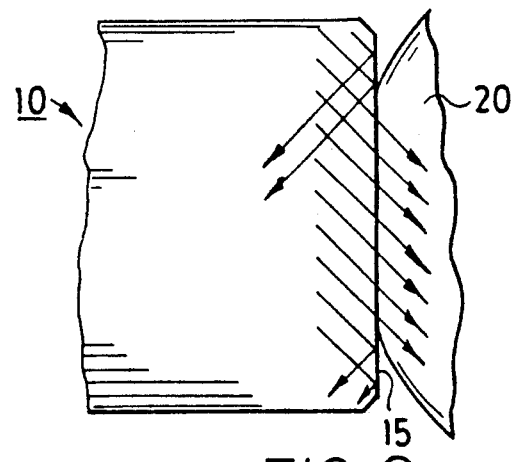
Figure 5:
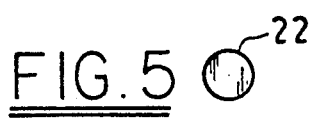
Figure 7:
Figure 6:
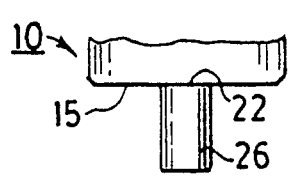
Figure 8:
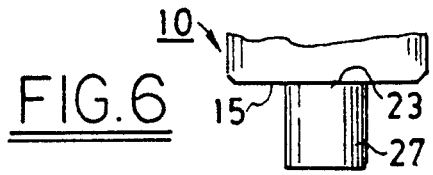

FIGS. 5 and 7 also respectively show the preferred reference and measurement applanation areas 22 and 23, taken respectively from the schematic side views of FIGS. 1 and 2. Although the areas of FIGS. 5 and 7 are shown as circular, the actual shape of the corneal area that is applanated by engagement with prism surface 15 can deviate from circular. Such deviation makes Goldman-type tonometers difficult to use, because split images of the applanated area have to be matched up; and the matching process requires judgment when the applanated area is not circular. A non-circular applanated area does not affect the accuracy of our tonometer, however, because light will transmit through the applanated area, regardless of its shape; and our detector is responsive to the size of the applanated area, and not its shape.

We prefer that the size of reference area 22 be smaller than the size of measurement area 23, but this also could be reversed. A smaller reference area 22 can be made slightly larger than the corneal applanation that occurs when applanating surface 15 is brought into unpressured contact with cornea 20, where the liquid surface tension forming a meniscus around the area of contact tends to hold prism 15 lightly against cornea 20. Very light pressure beyond initial contact can applanate a small area suitable for a reference size 22, which we prefer to have about a 1.8 square millimeter area and about a 1.5 mm nominal diameter. We then determine intraocular pressure by the force required to press prism 10 against cornea 20 sufficiently to applanate a larger measurement area 23, which we prefer to have about a 7.0 square millimeter area and about a 3.0 mm nominal diameter. Different sizes of reference and measurement areas can be used, but we prefer these sizes, for reliability and accuracy.

If the reference and measurement sizes 22 and 23 were reversed, or if the reference size 22 were otherwise made larger than measurement size 23, the measurement process would be similarly reversed. More pressure would be applied to applanate a larger reference size, and the pressure reduction required to applanate the smaller measurement size would be used to determine intraocular pressure.

Our tonometer is calibrated by contacting applanating surface 15 of prism 10 with calibrating elements 26 and 27. These transmit IR light and have contact surfaces respectively formed to the preferred 1.8 square millimeter size of reference area 22 and the preferred 7.0 square millimeter size of measurement area 23. The calibration surfaces 22 and 23 of elements 26 and 27 are wetted with water or artificial tears before contact with applanating surface 15 of prism 10. The index of refraction of elements 26 and 27 preferably approximates the 1.33 index of refraction of water and the human cornea so that their calibration surfaces 22 and 23 are similar to cornea 20 in the effect they have on the light that is internally incident on applanating surface 15. In other words, the light incident on surface 15 in the region of contact with a calibration surface is refractively transmitted into the calibration element and is not reflected to the detector.

A microprocessor that controls our tonometer, as explained in more detail below, can be set in a calibration mode so that the amount of light reflected to the detector when applanating surface 15 engages surface 22 of calibrating element 26 establishes the reference size of applanation area. Then, when the instrument prism contacts a cornea and the detector receives the calibrated reference amount of light, applanation of the cornea to the reference size area is assured. Similarly, in a calibration mode, applanating surface 15 of prism 10 is engaged with the wetted measurement surface 23 of calibration element 27 to calibrate the tonometer for the measurement size of applanation area. Then whenever the calibrated measurement amount of light reaches the detector while applanating surface 15 engages a cornea, applanation of the cornea to the desired measurement size is virtually certain.

Since calibration prepares the detector to determine accurately both the reference and measurement sizes of corneal applanation, intraocular pressure can be accurately determined from the force difference required to change between these two sizes of applanation area. We prefer a spring as a way of varying the force used in pressing prism 10 against the eye to determine such a force difference, but there are many other ways of possibly delivering the variable force. These include movable weights responsive to gravity, solenoids, piezoelectric drives, and other mechanical and electromechanical devices.

Figure 9:
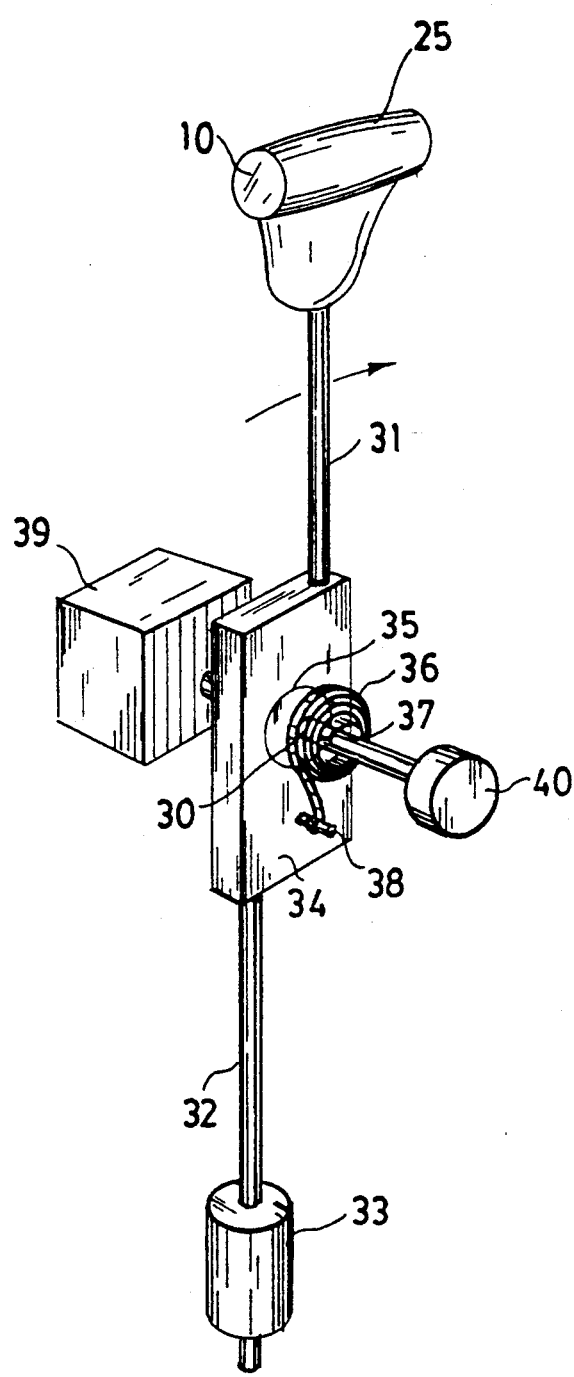

In a simple form illustrated partially schematically in FIG. 9, we prefer that prism 10 be held within a housing 25 mounted to pivot around an axis 30 so that prism 10 can be moved toward and away from an eye. An arm 31 extends upward from pivot axis 30 to support prism 10 and its housing 25. Another arm 32 extends on the opposite side of pivot axis 30 to support a counterbalance 33, which removes the influence of gravity upon the pivoting of prism 10.

We prefer that spring 36 be spiral wound like a clock spring, having one end anchored to a pin 38 on pivot block 34, which supports both arms 31 and 32 and pivots on a bearing 35 on axis 30. The other end of spring 36 is connected to a shaft 37 that can be rotated on axis 30 to change the spring force applied to pivot block 34 via spring pin 38. This in turn changes the force by which prism 10 within housing 25 is pressed against an eye.

There are also many ways that shaft 37 can be turned to change the position of spring 36 and the resulting force applied to press prism 10 against the eye. A thumb wheel is one possibility, and this can be arranged either directly driving shaft 37 or indirectly driving through reduction gearing. The illustrated possibility is a stepping motor 39 that is operated to turn shaft 37 in increments. Stepping motor 39 can also be arranged to turn shaft 37 through a reduction drive.

Regardless of how shaft 37 is turned to adjust the position of spring 36, it is necessary to keep track of the position of shaft 37, preferably with a microprocessor, for calculating the force variance from which the intraocular pressure is derived. The angular position of shaft 37 can be determined by decoder 40, which is preferably mounted on pivot axis 30 to sense the rotational position of shaft 37 and communicate this to a microprocessor. Other possibilities include a stepping motor drive that determines the angular position of shaft 37 from the rotational position of the motor.

Figure 10:
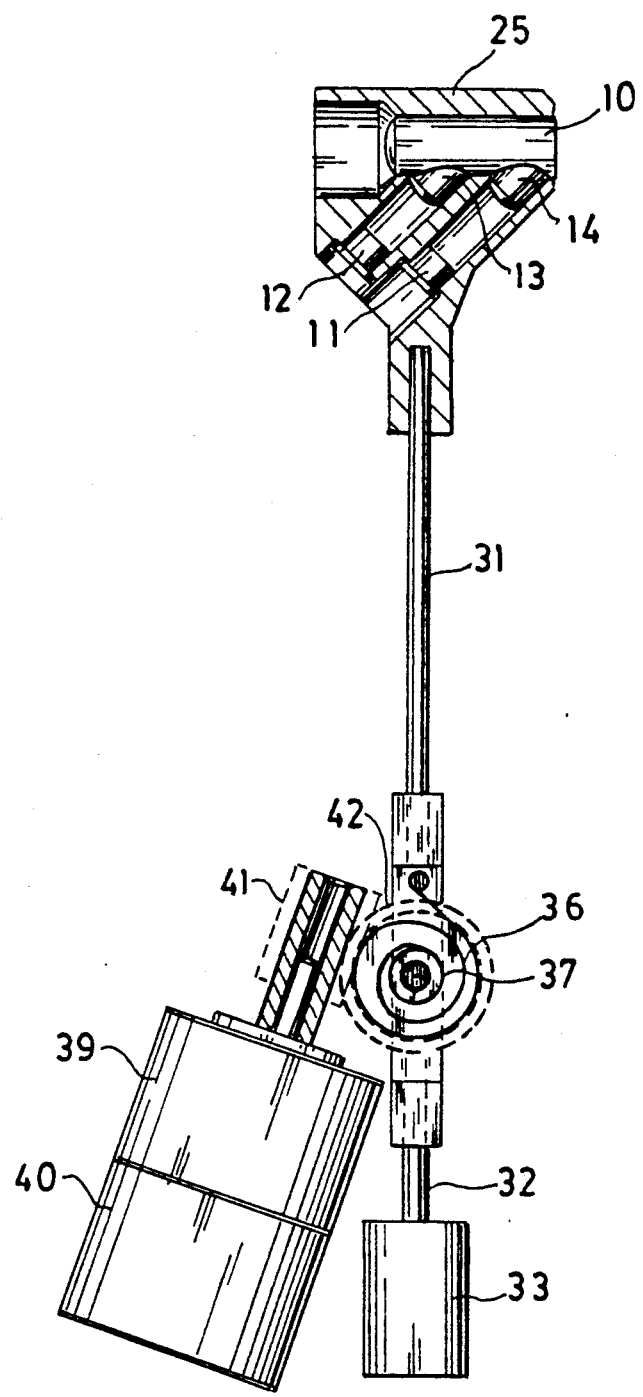

FIG. 10 shows a similar arrangement for applying variable force to applanating prism 10 mounted in housing 25 on pivot arm 31 counterbalanced by weight 33 on arm 32. A similar spiral spring 36 is mounted on a rotatable shaft 37 for applying pivot force to housing 25 and prism 10; and the change in position of spring 36 for varying the applanating pressure is provided by stepping motor 39, which rotates spring shaft 37 via a reduction drive formed of worm gear 41 and worm wheel 42. This reduction allows small rotational steps of motor 39 to turn spring shaft 37 by much smaller angular amounts for finely dividing the prism pressing force into increments usable in determining intraocular pressure. Different forms of reduction drives can be used for this. The rotational position of stepping motor 39 is monitored by decoder 40, so that a microprocessor can determine the variable force being applied to prism 10.

Figure 11:
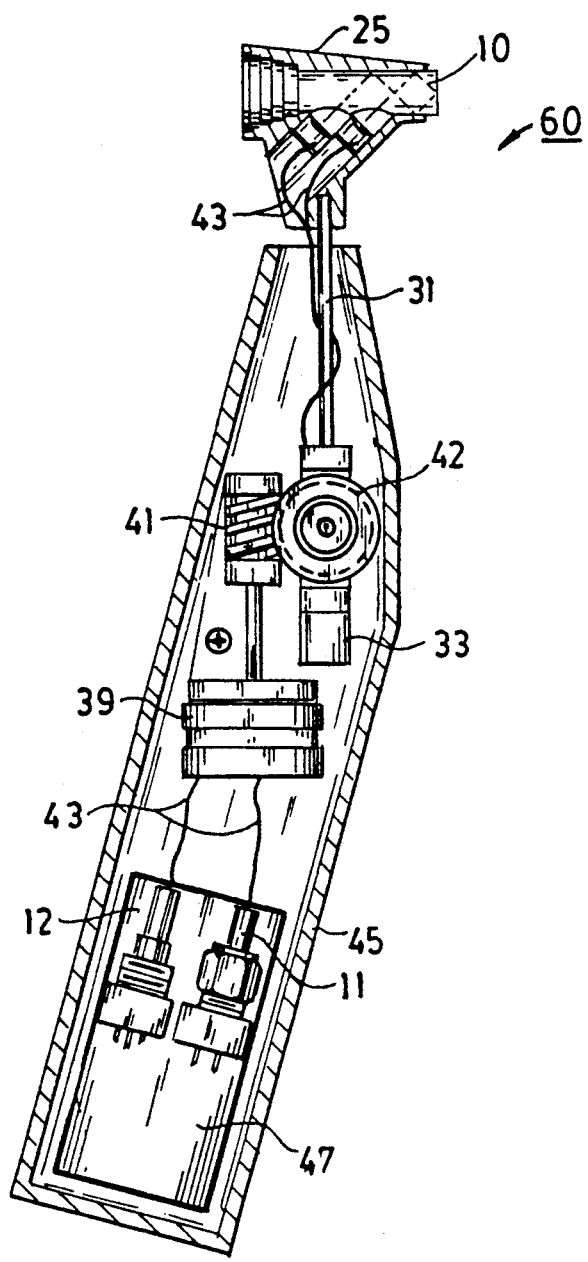
FIG. 11 shows a prism pressing system similar to those shown in FIGS. 9 and 10 arranged within a tonometer housing.

In FIG. 10, light source 12 and detector 11 are interchanged in position relative to ports 13 and 14 of prism 10, to illustrate this possibility. Since source 12 and detector 11 are mounted in prism housing 25, it is necessary for electric conductors to lead to a fixed region within the tonometer where signals can be processed. An alternative, as shown in FIG. 11, uses fiber optic light conductors 43 leading from a source 12 and a detector 11 that are arranged in communication with circuit board 47, disposed in a handle region 45 of tonometer 60. The mechanical drive for variably pressing prism 10 against the cornea is otherwise similar to the drive of FIG. 10.

Figure 12:
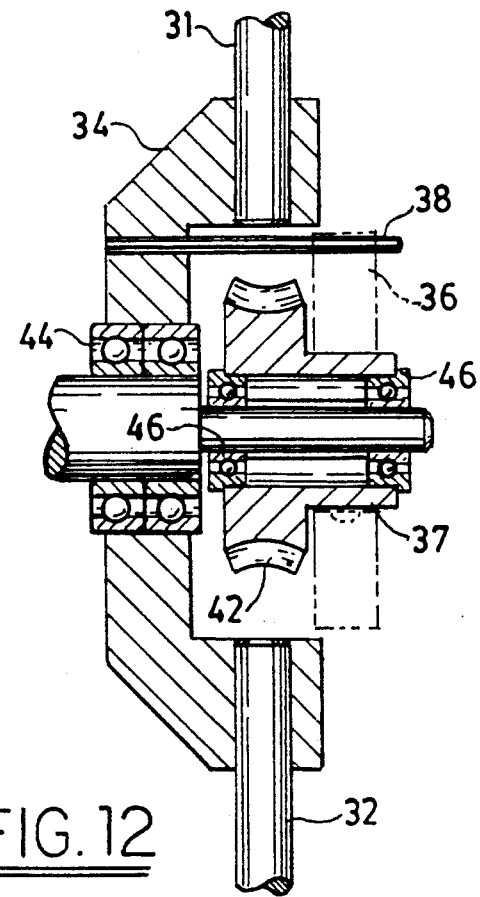
FIG. 12 shows an enlarged view of a spring-biased pivot hub usable in the tonometers of FIGS. 10 and 11.

A pivot hub suitable for the mechanical drives illustrated in FIGS. 10 and 11 is shown in FIG. 12. Pivot block 34 supporting arms 31 and 32 is mounted on bearing 44 so that arm 31 can pivot freely in response to the force of spring 36, which is applied to spring pin 38. The fixed end of spring 36 is secured to spring shaft 37, which is angularly turned by worm wheel 42. Bearings 46 support worm wheel 42 and spring shaft 37 so that worm wheel 42 can be rotated by a stepping motor or thumb wheel turning a worm gear that is not shown in FIG. 12.

Figure 13:
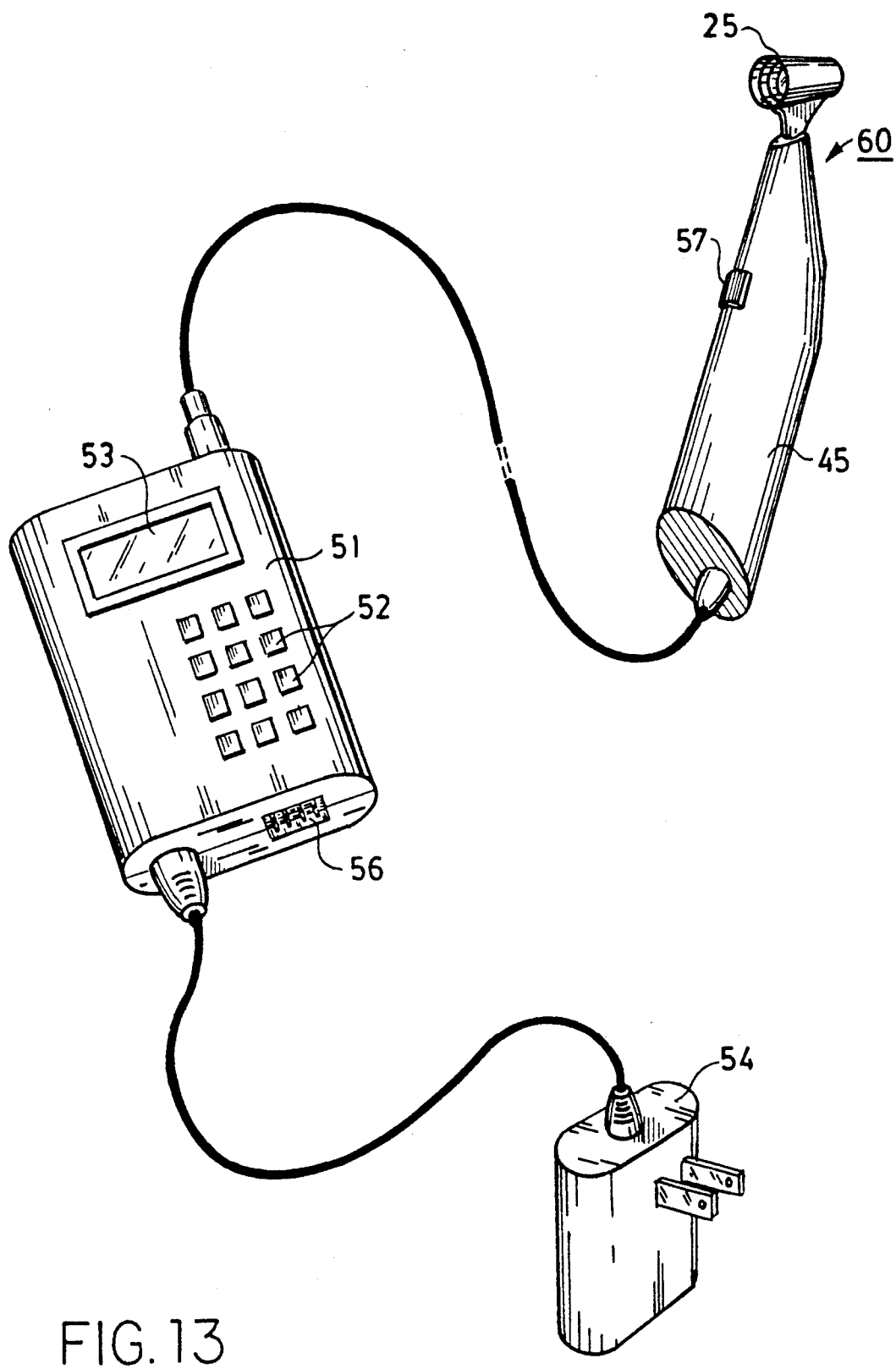
FIG. 13 shows a preferred embodiment of our tonometer combined with a microprocessor driven display.

Tonometer 60 is shown in FIG. 13 as it relates to a microprocessor, which can be arranged in handle region 45 or in portable case 51. Either way, as schematically shown in FIG. 14, microprocessor 50 preferably includes or communicates with memory and storage devices, is accessible via keyboard 52, and drives a display 53 where intraocular pressure and other information can be displayed. We prefer that tonometer 60 be portable, along with case 51, so we include battery charging device 54. We also prefer that microprocessor 50 be able to exchange information with a computer 55; and for this purpose, we have provided a computer interface connection 56 on portable case 51.

Tonometer 60 can be operated in a hand held position or while mounted on a frame, such as a slit lamp microscope frame. Since prism housing 25 is counterbalanced, tonometer 60 can be operated in any orientation, to measure the intraocular pressure of patients that are upright or prone, for example.

The pressures involved in variably pressing prism 10 against the cornea 20 are small enough, and the distances traveled by pivoting prism housing 25 are small enough so that our tonometer can operate accurately from a hand held position. It is only necessary for the user to steady the tonometer and bring the applanating surface of prism 10 into contact with the cornea and then press start switch 57, to initiate an intraocular pressure reading. The operating steps to accomplish this can occur in several different ways.

We prefer that prism housing 25 have a sufficient length of travel, relative to handle housing 45 so that a measurement sequence can be started, under control of microprocessor 50, when the applanating surface 15 of prism 10 is spaced a few millimeters from cornea 20. Tonometer 60 can then drive prism 10 forward into sufficient contact with the cornea to applanate the cornea to the reference size, which the detector can determine from previous calibration to that size. Then, the pressure of prism 10 against the cornea is increased until a measurement size area is applanated, again as determined by the calibrated detector. We prefer that several readings be made in rapid succession by moving prism 10 back and forth between reference and measurement sizes of applanation areas. Microprocessor 50 can then compare such readings, and calculate and display the average, along with the standard deviation of the readings. This process assumes a motor drive, which we prefer; but it can also be implemented manually by a thumb wheel drive.

Alternatively, the user can bring the applanating surface 15 of prism 10 into contact with cornea 20 before pressing start button 57 to initiate a series of readings made while prism 10 is shifted rapidly back and forth by varying pressures that change the applanation area between reference and measurement sizes. Microprocessor 50 can also be programmed for automatically initiating a measurement sequence when prism 10 is pressed against cornea 20 with sufficient pressure to applanate the reference size area. In fact, the operating process can be varied in several ways, to suit the convenience of the users; and the variations can include reversing or altering the sizes of the reference and measurement areas and applying the variable prism pressing force in different ways.

To add to the convenience of tonometer 10, we prefer that microprocessor 50 be able to store and display patient data and related information such as previous intraocular pressure measurements for patients. An ophthalmologist can then load microprocessor 50 with the relevant data from patients about to be examined and can have all the necessary information made available via display 53 as the examinations proceed. Meanwhile, the new measurements and the dates the measurements were made can be added to the data for each patient, to be fed later to computer 55.

Assuming operation such as described above, the potential variables include:

Po = Ocular pressure
N = Gear train ratio
n = Number of motor steps required to reach a specific applanation area
a = Motor rotation angle per step
T = Torque applied to the spring
$\phi$ = Rotation of sensor arm prior to eye contact
B = Spring deflection angle
B + $\phi$ = Total rotation angle of driven end of spring
K = T/B = Spring constant, i.e., lbs-in./rad.
R = Effective sensor arm length
F = Force of prism on cornea
A = Applanation area
A(ref) = Area @1.8 sq. mm
A(meas) = Area @7.0 sq. mm
n(ref) = Number of motor steps to 1.8 sq. mm applanation area
n(meas) = Number of motor steps to 7.0 sq. mm applanation area The torque applied to spring 36 for pressing prism 10 against the cornea can be expressed as:

$$T = B \times K = F \times R, \text{ or } B = F \times \frac{R}{K}$$

The intraocular pressure relative to the prism pressing force can be expressed as:

$$F = A \times Po$$

Or, in terms of spring rotation angle, B, the relationship can be expressed as:

$$B = A \times P_o \times \frac{R}{K}$$

In terms of rotation angles and motor steps, the relationship can be expressed as:

$N(B + \phi) = n(a)$ = Motor rotation angle, or $$n = (B + \phi) \times \frac{N}{a}, \text{ or}$$

$$n = \left(\left(A \times P_o \times \frac{R}{K}\right) + \phi\right) \times \frac{N}{a}$$

From this, the motor step values for the reference and measurement sizes of applanation areas can be subtracted to form an expression in terms of a computer program function as follows:

$$n(\text{meas}) - n(\text{ref}) = \left(\frac{N}{a}\right) \times \left(\frac{R}{K}\right) \times (A(\text{meas}) - A(\text{ref})) \times P_o$$

The "n" values for the number of motor steps or increments of angular rotation are the values that are measured, and the ocular pressure Po is the value determined. All other values in the equation are constant and are installed in the computer program. The light value readings for the reference and measurement sizes of the applanation area are stored in the program via the calibration process described above. From all this, microprocessor 50 can determine intraocular pressure from the angular positions of spring shaft 37 at the reference and measurement sizes of corneal applanation.

The result is a tonometer 60 that is completely objective and correspondingly reliable in making intraocular pressure readings. The readings can be done rapidly under control of a microprocessor, with minimal user skill required. The microprocessor involved also allows easy display and manipulation of patient data, storage of relevant information, and communication with a computer so that the instrument quickly and readily provides any desired function.

We claim:

1. An applanation tonometer having an applanating prism with an optical surface larger than an area of said cornea to be applanated by said optical surface; a light source arranged for directing light toward the optical surface; a light detector arranged for detecting a portion of said light; a variable force element arranged for pressing said optical surface of said prism against said cornea with varying pressure capable of changing the size of an applanated area of said cornea; and an indicator responsive to said detector and said variable force element for indicating intraocular pressure as a function of force applied in pressing said prism against said cornea, said tonometer further comprising:

a. said light source being arranged for directing said light toward the optical surface at an incidence angle that divides the incident light into a transmitted portion and a reflected portion, said transmitted portion passing through said optical surface in an interface area where said optical surface is adapted to engage and applanate said cornea and said reflected portion reflecting from said optical surface in an area around said interface area;

b. said detector being arranged relative to said optical surface so that the amount of one of said light portions reaching said detector varies as a function of the size of said applanated interface area; and c. said variable force element being arranged so that the prism pressing force applied to indicate intraocular pressure is the force required for changing the size of said applanated interface area between a reference size and a measurement size, said reference and measurement sizes being identified by said detector from the amounts of the light portion reaching said detector.

2. The tonometer of claim 1 wherein said light source directs light toward the eye through said prism, the transmitted light portion passing through said optical surface is absorbed by the eye, and the reflected portion is reflected back to said detector.

3. The tonometer of claim 2 wherein said prism is configured to provide internal light paths from said source to said optical surface and from said optical surface to said detector.

4. The tonometer of claim 1 wherein said variable force element comprises a spring arranged for pressing said prism against said cornea and means for varying the position of said spring.

5. The tonometer of claim 4 wherein said position varying means comprises a stepping motor.

6. The tonometer of claim 1 wherein said indicator responds to variation in position of a spring arranged for pressing said prism against said cornea, for determining said intraocular pressure.

7. The tonometer of claim 6 including a rotatable element for varying said spring position.

8. The tonometer of claim 1 wherein said reference size is smaller than said measurement size.

9. The tonometer of claim 1 including a microprocessor and a display arranged for storing and displaying patient information relating to said intraocular pressure.

10. A method of measuring intraocular pressure by using an applanation tonometer having a prism with an optical surface that is variably pressed against a corneal surface of the eye to applanate an area of said corneal surface, said method comprising:

a. a directing light toward said eye so that light is incident on said optical surface at an incidence angle that divides the incident light into transmitted and reflected portions, said transmitted portion passing through an interface area of said optical surface where said optical surface is in applanating contact with said corneal surface and said reflected portion reflecting from said optical surface in an area outside said interface area, said light portions varying as functions of the size of said applanated interface area;

b. detecting one of said light portions;

c. changing the size of said applanated interface area between a reference size and a measurement size represented by differences in the amount of the detected light portion; and d. determining intraocular pressure of said eye from the force difference required for changing said applanated interface area between said reference and measurement sizes.

11. The method of claim 10 including directing said light toward said eye through said prism and detecting said reflected portion.

12. The method of claim 10 including changing the position of a spring as a way of pressing said prism against said corneal surface with variable force.

13. The method of claim 12 including using a stepping motor for changing the position of said spring.

14. The method of claim 10 including using different positions of a spring pressing said prism against said corneal surface as a way of determining said force difference required to achieve said reference and measurement sizes of said applanated area.

15. The method of claim 14 including using a rotatable element for changing positions of said spring.

16. The method of claim 10 including calibrating said tonometer by engaging said optical surface with calibration surfaces in said reference and measurement sizes.

17. The method of claim 10 including making said reference size smaller than said measurement size.

18. The method of claim 10 including using a microprocessor to store, display, and communicate said intraocular pressure.

19. A method of determining intraocular pressure by variably pressing a prism against a cornea for applanating an area of said cornea, said method comprising:
   a. using a force responsive device for varying the pressure of said prism against said cornea for sequentially applanating a reference area and a different sized measurement area of said cornea;
   b. determining the prism pressing force difference required to change the cornea applanation area size between said reference area and said measurement area, said prism pressing force difference being a function of said intraocular pressure; and
   c. determining said reference and measurement area sizes by directing light toward a cornea-contacting surface of said prism at an incidence angle that divides the light into a transmitted portion passing through said prism surface in the applanated area and a reflected portion around the applanated area that reflects from said prism surface, and detecting the amount of one of said portions as representing the size of the applanated area.

20. The method of claim 19 including varying the position of a spring serving as said force responsive device.

21. The method of claim 20 including turning a rotatable element for varying the position of said spring. and determining said prism pressing force by the position of said rotatable element.

22. The method of claim 19 including directing said light through said prism to be incident on said prism surface and detecting said reflected portion.

23. The method of claim 22 including predetermining said amount of said difference in said reflected light between said reference and measurement areas by contacting said optical surface with calibration surfaces in said reference and measurement sizes.

24. The method of claim 19 including moving an element of said force responsive device for varying said prism pressing force.

25. The method of claim 24 including manually moving said element of said force responsive device.

26. The method of claim 24 including electrically moving said element of said force responsive device.

27. The method of claim 19 including making said reference area smaller than said measurement area.

28. The method of claim 19 including digitally processing said intraocular pressure for display, storage, and communication with a computer.

29. In an applanation tonometer having a prism surface adapted to be pressed against the cornea of an eye with a variable force so that said prism surface applanates a varying area of said cornea, the improvement comprising:
   a. a source of light directed toward said prism surface so that said light is divided between a portion that transmits through said prism surface in an applanation area where said prism surface is adapted to engage and applanate said cornea and a portion that reflects from said prism surface outside of said applanation area;
   b. a light detector arranged for detecting the amount of one of said portions in a region spaced from said prism surface, the detected light portion varying as a function of the size of said applanation area; and
   c. a prism pressing force determiner arranged for indicating intraocular pressure as a function of the prism pressing force required to applanate said cornea to a predetermined size of said applanation area.

30. The improvement of claim 29 wherein said prism is configured to provide a path for said light from said source to said prism surface and a path for light reflected from said prism surface to said detector.

31. The improvement of claim 29 wherein light transmitted through said prism surface enters said eye and does not reflect back to said detector.

32. The improvement of claim 29 including a spring arranged for supplying said prism pressing force.

33. The improvement of claim 32 including movable means for varying the position of said spring to vary said prism pressing force.

34. The improvement of claim 33 wherein said prism pressing force is determined from the position of said movable element.

35. The improvement of claim 29 wherein said prism pressing force is the force required to change between detected reference and measurement sizes of said applanation area.

36. The improvement of claim 35 wherein said reference size is smaller than said measurement size.

37. The improvement of claim 35 including calibration surfaces in said reference and measurement sizes arranged so that said prism surface can engage said calibration surfaces for calibrating said tonometer.

38. The improvement of claim 35 wherein said light detector is arranged for determining said reference and measurement sizes of said applanation area from different amounts of said reflected light portion.

39. The improvement of claim 29 wherein said light from said source is incident on said prism surface at an angle that divides said light between said transmitted portion and said reflected portion.

40. The improvement of claim 29 including a microprocessor arranged for determining intraocular pressure in response to said light detector and said prism pressing force determiner.

41. The improvement of claim 40 including a display operable by said microprocessor, and a communication port enabling said microprocessor to communicate with a computer.

42. An applanation area size determiner for an applanation tonometer having a prism surface adapted to be pressed against the cornea of an eye with a variable force so that the prism surface applanates a varying area of the cornea, said applanation area size determiner comprising:

a. said prism being configured to direct light from a source to be incident on said prism surface at an incidence angle that causes light incident in the applanation area to pass into said eye and causes light incident in an area around the applanation area to reflect from said prism surface; and b. a detector arranged for detecting light reflected from said prism surface around the applanation area for determining a size of said applanation area from the amount of said reflected light.

43. The determiner of claim 42 wherein said light is infrared.

44. The determiner of claim 42 wherein said detector includes means for detecting a reference size and a measurement size.

45. The determiner of claim 44 wherein said reference size is smaller than said measurement size.

46. The determiner of claim 44 including calibration surfaces formed in said reference and measurement sizes to be engaged with said prism surface for calibration purposes.

47. The determiner of claim 42 wherein said prism is formed of a material having an index of refraction of about 1.5.

48. The determiner of claim 47 wherein said light is infrared and said incidence angle is about 45°.

49. The determiner of claim 42 wherein said prism is configured with a mirror surface for directing said light onto said prism surface and for directing said reflected light onto said detector.

* * * * *